US006947039B2

(12) United States Patent
Gerritsen et al.

(10) Patent No.: US 6,947,039 B2
(45) Date of Patent: Sep. 20, 2005

(54) METHOD, SYSTEM AND COMPUTER PROGRAM FOR PRODUCING A MEDICAL REPORT

(75) Inventors: Frans Andreas Gerritsen, Eindhoven (NL); Roel Truyen, Eindhoven (NL); Iwo Willem Oscar Serlie, Delft (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 242 days.

(21) Appl. No.: 10/143,640

(22) Filed: May 10, 2002

(65) Prior Publication Data

US 2002/0190980 A1 Dec. 19, 2002

(30) Foreign Application Priority Data

May 11, 2001 (EP) .......................................... 01201742

(51) Int. Cl.[7] .............................................. G06T 15/00
(52) U.S. Cl. ...................... 345/419; 345/424; 345/427; 345/629; 382/128; 600/427
(58) Field of Search ................................ 345/419, 424, 345/629, 427, 848; 382/128; 600/427

(56) References Cited

U.S. PATENT DOCUMENTS

| 5,611,025 | A | * | 3/1997 | Lorensen et al. ........... 345/419 |
| 6,167,296 | A | * | 12/2000 | Shahidi ...................... 600/427 |
| 6,380,958 | B1 | * | 4/2002 | Guendel et al. ............ 345/848 |
| 6,697,067 | B1 | * | 2/2004 | Callahan et al. ............ 345/427 |
| 6,785,410 | B2 | * | 8/2004 | Vining et al. ............... 382/128 |

FOREIGN PATENT DOCUMENTS

WO    WO0124116    5/2001 .......... G06T/17/40

OTHER PUBLICATIONS

Wegenkittl et al: "Mastering interactive virtual bronchioscopy on a low–end ps" Proceedings IEEE Visualization Conference 2000, pp. 461–464.

"Freeflight: A Virtual Endoscopy System" by Vining et al., CVRMed MRC AS 1997 First Joint Conf Computer Vision Virtual Reality, pp. 413–416.

"Mastering Interactive Virtual Bronchioscoy on a Low–End pc" by Wegenkittl et al in Proc. IEEE Visualization Conf. 2000, pp. 461–464, ACM Press, 2000.

"Quicktime VR– an image based approach to virtual environment navigation", by S.E. Chen, SIGGRAPH 95, held on Aug. 6–11, 1995, Los Angeles, CA, USA, Conference Proceedings, Annual Conference Series, pp. 29–38.

* cited by examiner

*Primary Examiner*—Kimbinh T. Nguyen

(57) ABSTRACT

The invention refers to a method of producing a medical report comprising a dynamic image information based on a volumetric scan of one or more internal organs of a subject. According to the method two-dimensional images for simulating a three-dimensional view of the one or more internal organs based on the volumetric scan are calculated using a workstation. The resulting two-dimensional images are next projected on a surface of a geometrical object, which is then unfolded to a two-dimensional flat plane (U,L,F,R,B,D), and stored in a generated textual medical report for further analysis on a low-end computer. Advantageously the stored two-dimensional images are displayed dynamically within the medical report, either as a sequence of images or as a part of a virtual environment.

12 Claims, 1 Drawing Sheet

METHOD, SYSTEM AND COMPUTER PROGRAM FOR PRODUCING A MEDICAL REPORT

BACKGROUND OF THE INVENTION

The present invention relates to a method of producing a medical report based on a volumetric scan of one or more internal organs of a subject, said method comprising the steps of a) calculating two-dimensional images for simulating a three-dimensional view of the one or more internal organs based on the volumetric scan; b) storing one or more of the two-dimensional images; and c) incorporating one or more of the stored two-dimensional images in the medical report.

Such a method is known from the article "FreeFlight: A Virtual Endoscopy System" by Vining et al., CVRMed MRC AS 1997 First Joint Conf. Computer Vision Virtual Reality, pages 413–416.

The known method concerns a virtual medical examination technique of a human patient. Based on a volumetric scan of said patient, for instance generated by means of Computed Tomography, and by means of virtual reality techniques a medically skilled person can examine the internal organs of the patient without the need for invasive examination. The three-dimensional view is usually displayed on a powerful computer, such as a workstation. A first medically skilled person can evaluate the three-dimensional view for different purposes, such as diagnosis, preparing interventional procedures and rehearsing surgical operations. In case of a diagnosis the textual part of the diagnosis is incorporated in a medical report for review on a low-end computer by a second medically skilled person. To visualize the diagnosis the text is usually accompanied by static screenshots of areas of interest to which the diagnosis refers.

The known method has the disadvantage that the second medically skilled person reviewing the medical report, which is usually an interventional physician, receives only limited information with a static character and misses the full viewing interaction that was available to the first medically skilled person making the diagnosis.

It is an object of the method according to the invention to produce a medical report with more information which is still suitable for review on a low-end computer.

The method according to the invention is therefore characterized in that the method further comprises the steps of:

d) Providing a dynamical display of the stored two-dimensional images for simulating at least part of the three-dimensional view; and e) Incorporating the dynamical display of the two-dimensional images in the medical report.

Advantageously the large computations involving the calculation of the two-dimensional images can be performed on a suitable high power computer first and the resulting medical report incorporating the stored two-dimensional images can then be transferred to a low-end computer for review. By dynamically displaying the stored two-dimensional images the reviewer keeps the possibility to look around in at least part of the simulated three-dimensional view thus receiving important extra information.

It is noted that method steps a) through d) are known per se from the article "Mastering Interactive Virtual Bronchioscopy on a Low-End pc" by Wegenkittl et al in Proc. IEEE Visualization Conf. 2000, pages 461–464, ACM Press, 2000. This method, however, refers only to the medical examination of the trachea of a patient based on a volumetric scan thereof and is not used for producing a medical report.

According to a first preferred embodiment of the method according to the invention step d) further comprises the step of displaying the stored two-dimensional images in a sequence. This way the reviewer is given the impression to be immersed in the three-dimensional environment as if he or she could "fly through it".

According to a second preferred embodiment of the method according to the invention step d) further comprises the steps of calculating a virtual environment based on the stored two-dimensional images at one or more viewpoints in the three-dimensional view; and allowing interactive inspection of the virtual environment. This embodiment provides the user the possibility to dynamically inspect the environment of a viewpoint interactively.

In a further preferred embodiment of the method according to the invention step b) for one or more viewpoints further comprises the steps of: projecting a number of two-dimensional images visible in different directions from a view point of the three-dimensional view onto the corresponding sides of an object; unfolding the object in two dimensions; and storing the two-dimensional unfolded object image. The thus calculated and stored images are suitable for processing by a low-end computer. Preferably the object is a cube. This allows for an intuitive view of the patient data in two dimensions.

In yet a further preferred embodiment the method further comprises the step of folding up the object image, thus forming the virtual environment. The already available information is now efficiently used to recreate the virtual environment for each viewpoint marked as important by the first medically skilled person producing the medical report.

According to another preferred embodiment of the method according to the invention slips with additional image information are added to the borders of a number of the sides of the object. Preferably the slips comprise duplicate image information. This embodiment assures that practically all information is visible and no vital information is inadvertently lost by defining the borders or edges of the object onto which the two-dimensional images are projected or mapped. This is especially an advantage when the internal organ under examination has an irregular surface, as is e.g. the case with the colon wall. Vital information about polyps or cancer could be hidden in the convolutions thereof. By using this embodiment the complete information becomes visible to a very high degree of nearly 100%.

In yet another preferred embodiment the method further comprises the steps of:

f) editing and/or analyzing a number of the images; and g) adding the edited and/or analyzed images to the medical report. The step of editing may comprise all sorts of processing of the subject data performed by a skilled person, such as defining a cross section through one or more of the internal organs of the subject. The step of analyzing may comprise all sorts of processing of the subject data performed by a skilled person, such as measuring at least part of the internal organs. This advanced embodiment offers the important possibility of extending the medical report with additional information based on the expertise and knowledge of the first medically skilled person.

The invention further refers to a system to carry out the method according to the invention, comprising a data acquisition device comprising means for recording the volumetric scan, which data acquisition system is connected to at least one high-end computer with high computational power, which high-end computer comprises means for producing the medical report and is connected to at least one low-end computer, which low-end computer comprises means for displaying the medical report.

The invention also concerns a computer program to carry out the method according to the invention.

BRIEF DESCRIPTION OF THE DRAWINGS

The invention will be further explained by means of the attached drawing, in which.

DETAIL DESCRIPTION OF THE INVENTION

Figure 1:
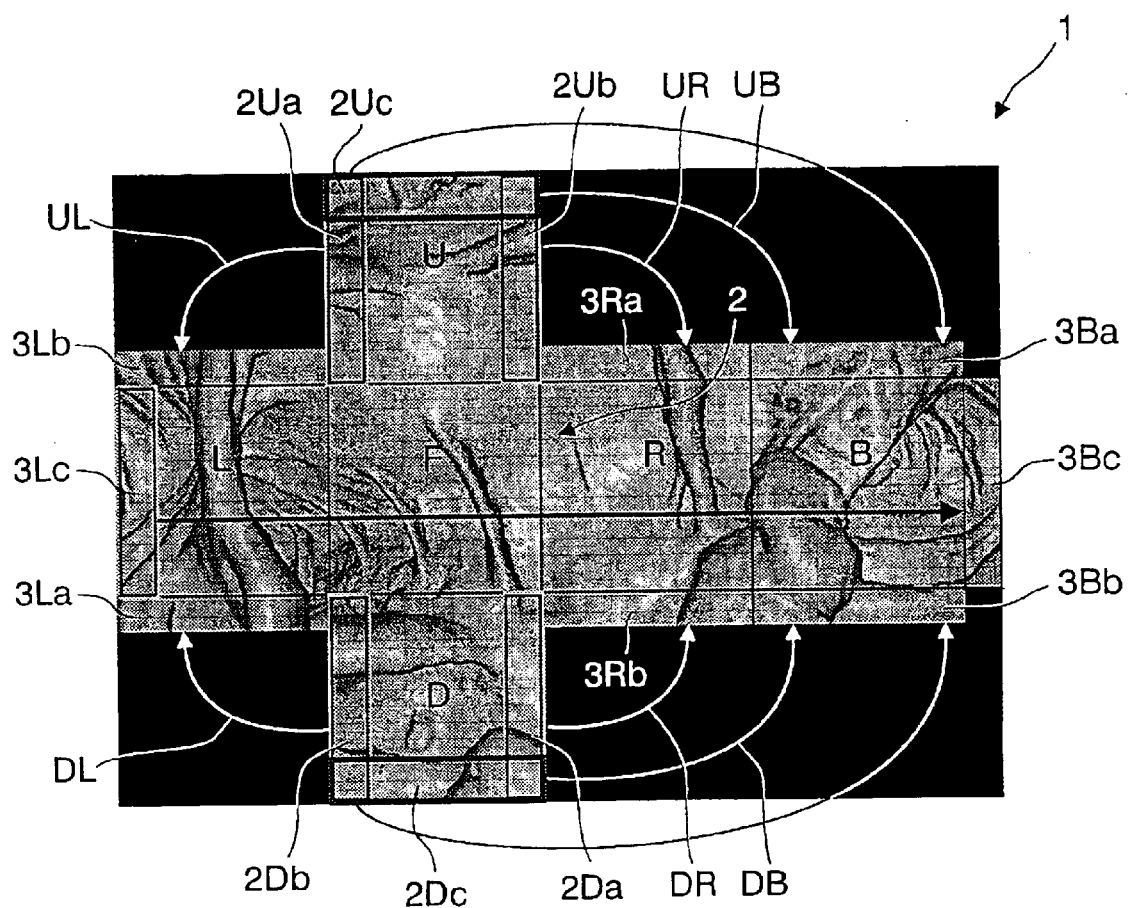
FIG. 1 shows an example of a two-dimensional image as part of a dynamical display incorporated in a medical report produced by means of the method according to the invention.

In general the method according to the invention refers to virtual medical examination techniques for examination of a subject, which is usually a human patient, but can also for instance be an animal. Said techniques allow an inner or outer view of hollow structures of the subject, e.g. organs, blood vessels, etc., by means of computer graphics. A virtual camera is placed in a three-dimensional data volume representing (part of) the subject. The method according to the invention will now be described according to a preferred embodiment, which relates to virtual endoscopy performed on a human patient.

In order to acquire the 3D patient data several known medical examination techniques can be used, which are also generally referred to as "volumetric scans", such as computed tomography (CT) or magnetic resonance tomography (MR). The 3D data are visualized by means of known virtual reality techniques. For this purpose different suitable rendering techniques are known in the field of computer graphics. Preferably use is made of Iso-surface volume rendering techniques, which are for instance described in the article "Iso-surface volume rendering", by M. K. et al., Proc. of SPIE Medical Imaging '98, vol. 3335, pp 10–19. Thus a virtual environment is created that simulates endoscopy.

These virtual reality techniques require extensive computations since the three-dimensional view is simulated by two-dimensional images that are to be calculated for each new viewpoint, e.g. by means of perspective rendering techniques. In order to perform these calculations and to show the resulting virtual environment with a sufficiently high image quality a computer with high computational power, such as a workstation, is usually used.

When evaluating the three-dimensional view the first medically skilled person stops at each view point showing important information and decides whether or not the information is to be incorporated in the medical report and gives the corresponding instructions.

According to the invention two-dimensional images resulting from the rendering techniques described above are projected or mapped onto a plane or the sides of an object. The object is next unfolded in two-dimensions and stored. The resulting stored two-dimensional unfolded object image simulates a three-dimensional view from a viewpoint from within the object. The first medically skilled person evaluating the patient data and making up the medical report decides which viewpoints contain important information and should be incorporated in the medical report. The number of selected viewpoints is unlimited. For each selected view point a two-dimensional unfolded object image is created as described above, stored and incorporated in the medical report.

Various different objects can be used to map the environment on, such as a cube, a sphere, a cylinder, etc. Suitable projecting or mapping techniques are known per se in the field of computer graphics. The two-dimensional unfolded object images can be stored in different formats, for instance a general format, such as jpeg or a specific format, such as a Quicktime VR-format. The resulting two-dimensional unfolded object images comprise a lot of information, but are suitable for display on a low-end computer.

An example of a stored two-dimensional unfolded object image resulting from the above projecting is shown in FIG. 1. Image 1 shows the inner colon wall of a patient. As can be clearly seen the originally two-dimensional images simulating the three-dimensional view are mapped on the sides of a cube 2, which is then folded open in two dimensions. The six sides of the cube are denoted as front (F), left (L), right (R), back (B), up (U) and down (D). This way the user is given an intuitive representation of the originally 3D information.

Preferably slips 3 with additional information are added to the borders of a number of the sides of the cube. Preferably these slips comprise duplicate information. Generally the slips comprise information of adjacent sides of the cube. In the embodiment shown slips are added to the borders of the left, right and backside of the cube 2. The added slips comprise information of areas defined in the up (U) and down (D) side of the cube. The dimensions of said areas correspond to the dimensions of the added slips. Said areas are referred to as slip areas. In the detailed embodiment shown the information of slip area 2Ua is copied to added slip 3Lb as is indicated by the arrow UL. The information of slip area 2Ub is copied to added slip 3Ra as is indicated by the arrow UR. The information of slip area 2Uc is copied to added slip 3Ba as is indicated by the arrow. The information of slip area 2Ub is copied to added slip 3Ra as is indicated by the arrow UR. Analogously the information of slip area 2Da is copied to added slip 3Rb as is indicated by the arrow DR. The information of slip area 2Db is copied to added slip 3La as is indicated by the arrow DL. The information of slip area 2Dc is copied to added slip 3Bb as is indicated by the arrow DB. A single arrow denotes a rotation over approximately 90 degrees whereas a double arrow denotes a rotation over approximately 180.

According to the invention the two-dimensional unfolded object images, such as image 1 in FIG. 1, which are also referred to as stored two-dimensional images, are incorporated in the medical report and displayed dynamically. For example the stored two-dimensional images can be displayed one after the other in a sequence. As a result of this dynamical display the user is given the impression to be immersed in the environment. The resulting extended medical report can be displayed on a so-called "low-end" computer, i.e. a computer with less computational power, such as a personal computer, for (re)simulating at least part of the three-dimensional view that was shown earlier by the high-end computer.

Another example of dynamically displaying the stored two-dimensional images comprises forming a virtual environment based on the stored two-dimensional images at one or more viewpoints in the three-dimensional view and allowing interactive inspection of the virtual environment. One practical and elegant way of forming the virtual environment is by folding up the object image. This can be performed by means of image based rendering techniques, which are known per se in the field of computer graphics. An example thereof is described in the article "Quicktime VR—an image based approach to virtual environment navigation", by S. E. Chen, SIGGRAPH 95, held on 6–11 Aug. 1995, Los Angeles, Calif., USA, Conference Proceedings, Annual Conference Series, pp29–38.

The forming of the virtual environment can be used as an alternative to or in combination with the above described sequential display, both being ways of dynamically displaying the stored two-dimensional images.

According to the invention the patient data processed by means of the above-described rendering techniques are included in the medical report together with accompanying text, such as the textual part of a diagnosis. The resulting extended medical report thus comprises the text together with the visual environment, in which the user, usually a second medically skilled person, such as a physician, can interactively inspect the patient data on a low-end computer, while keeping full interactivity. Such an extended report helps the user to make medical judgements, for instance as to shape, position and spatial environmental relations of any abnormalities found.

Preferably means are provided to add additional information to the extended report. Generally the additional information can comprise the result of analysis or editing of the images. Some examples of additional information are: an overview image with the locations of suspicious areas; multiplanar reformats at the position of the suspected abnormality or lesion; measurements of (part of) the internal organs and annotations.

The method according to the invention is preferably carried out by a computer program. The means for incorporating additional information to the report can then be activated by a click on a corresponding button on the computer. For example, during inspection of the patient data the user (the first medically skilled person) has the option to press the so-called "add to report button" each time he or she suspects a lesion or abnormality. In the preferred embodiment the entire surroundings are then automatically incorporated in the medical report together with an overview image displaying the location.

Figure 2:
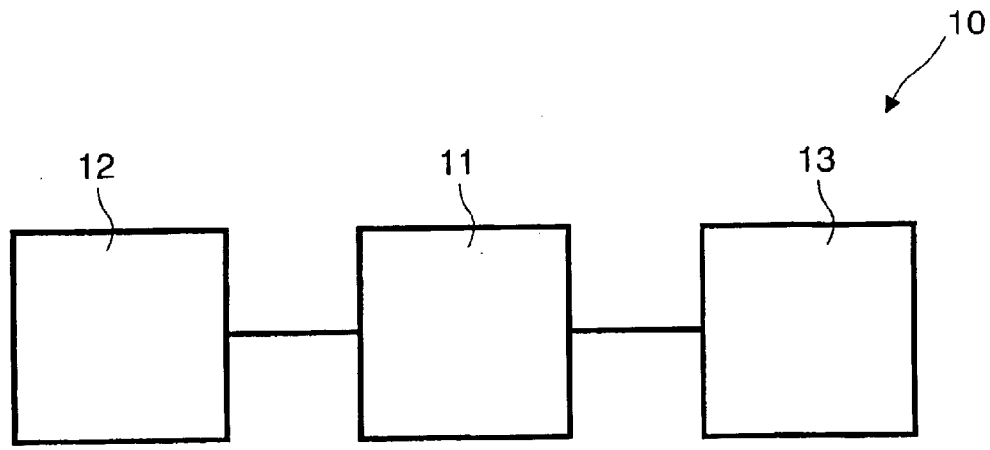
FIG. 2 schematically shows a system for carrying out the method according to the invention.

The system requirements for carrying out the method of the invention are as follows. A suitable system 10 for performing the method by means of the computer program is schematically shown in FIG. 2. System 10 should comprise at least one high-end computer 11 having high computational power, such as a workstation, connected to at least one low-end computer 12, such as a personal computer. The connection can be established by any suitable means, for instance an internet or intranet connection. The high-end computer 11 is preferably coupled to the data acquisition system 13 for acquiring the subject data. The subject data set can be acquired by means of various techniques, such as 3D X-ray rotational angiography, computed tomography, magnetic resonance imaging or magnetic resonance angiography.

Now the method of the invention is explained a skilled person will be able to translate the steps of the method into a computer program to carry out the method. The steps of such a computer program involving extensive calculations are performed on the high performance computer. Among these are the steps of calculating two-dimensional images for simulating a three-dimensional view of the one or more internal organs based on the volumetric scan and storing one or more of the two-dimensional images, which can for example be carried out by means of perspective volume rendering techniques. The step of providing a dynamical display of the stored two-dimensional images for simulating at least part of the three-dimensional view for producing an inner view of the one or more internal organs can be carried out on the low-end computer using image based rendering techniques. On the market suitable software is available per se for displaying a sequence of images or a virtual environment surrounding a viewpoint.

The resulting extended medical report is saved in an appropriate format. The complete report can be saved in a hypertext format, such as the widely known html-format. The dynamical displays can be incorporated in the report by formats suitable for sequences, such as mpeg, avi, qtvr or by formats that allow viewing virtual environments, such as vrml or qtvr. The extended report is then transferred to the low-end computer for review. The low-end computer needs to have a browser and a plug-in suitable for handling the specific kind of format of the extended medical report and accompanying dynamical display of two-dimensional images. Various different software applications are available on the market from which a skilled person can choose.

The invention is of course not limited to the described or shown embodiment, but generally extends to any embodiment, which falls within the scope of the appended claims as seen in light of the foregoing description and drawings.

What is claimed is:

1. A method of producing a medical report based on a volumetric scan of one or more internal organs of a subject, said method comprising the steps of:
   a) Calculating one or more two-dimensional images for simulating a three-dimensional view of the one or more internal organs based on the volumetric scan;
   b) Projecting one or more two-dimensional images visible in different directions from a view point of the three-dimensional view onto corresponding sides of an object which are denoted to provide an intuitive representation of the three-dimensional view, unfolding the object in two dimensions, and storing the two-dimensional unfolded object image;
   c) Incorporating at least one two-dimensional unfolded object image into the medical report;
   d) Providing a dynamical display of at least one two-dimensional unfolded object image for simulating at least part of the three-dimensional view; and
   e) Incorporating the dynamical display of at least one two-dimensional unfolded object image in the medical report.

2. Method according to claim 1, wherein step d) further comprises displaying the stored two-dimensional images in a sequence.

3. Method according to claim 1, wherein step d) further comprises forming a virtual environment based on the stored two-dimensional images at one or more viewpoints in the three-dimensional view and allowing interactive inspection of the virtual environment.

4. Method according to claim 1, wherein the object is a cube.

5. Method according to claim 3, wherein the method further comprises a step of folding up the object image, thus forming the virtual environment.

6. Method according to claim 1, wherein slips with additional image information are added to the borders of a number of the sides of the object.

7. Method according to claim 6, wherein the slips comprise duplicate image information.

8. Method according to claim 1, further comprising the steps of:

f) editing and/or analyzing a number of the images; and g) adding the edited images and/or the analysis to the medical report.

9. System to carry out the method according to claim 1, comprising a data acquisition device including means for recording the volumetric scan, which data acquisition system is connected to at least one high-end computer, which high-end computer comprises means for producing the medical report and is connected to at least one low-end computer, which low-end computer comprises means for displaying the medical report.

10. Computer program to carry out the method according to claim 1.

11. Method according to claim 1, wherein the object is a cylinder.

12. Method according to claim 1, wherein the object is a sphere.

* * * * *